(12) United States Patent
Kolberg et al.

(10) Patent No.: US 8,721,558 B2
(45) Date of Patent: May 13, 2014

(54) DEVICE FOR DETERMINING THE FLOW RATE OF A BLOOD FLOW, AND CARDIOVASCULAR ASSIST DEVICE

(75) Inventors: Gernot Kolberg, Berlin (DE); Klaus Bartels, Berlin (DE)

(73) Assignee: BIOTRONIK CRM Patent AG (CH)

( * ) Notice: Subject to any disclaimer, the term of this patent is extended or adjusted under 35 U.S.C. 154(b) by 1108 days.

(21) Appl. No.: 12/508,706

(22) Filed: Jul. 24, 2009

(65) Prior Publication Data

US 2010/0022899 A1    Jan. 28, 2010

(30) Foreign Application Priority Data

Jul. 28, 2008   (DE) .......................... 10 2008 040 788

(51) Int. Cl.
*A61B 5/02* (2006.01)

(52) U.S. Cl.
USPC ............. 600/505; 600/504; 600/506; 600/16; 600/17; 607/17

(58) Field of Classification Search
USPC ................. 600/505, 506, 504, 16, 17; 607/17
See application file for complete search history.

(56) References Cited

U.S. PATENT DOCUMENTS

| | | | |
|---|---|---|---|
| 3,902,501 A * | 9/1975 | Citron et al. .................. | 607/126 |
| 5,602,342 A | 2/1997 | Strandberg | |
| 5,799,350 A | 9/1998 | Ferek-Petric et al. | |
| 6,299,583 B1 * | 10/2001 | Eggers et al. ................. | 600/526 |
| 6,738,667 B2 | 5/2004 | Deno et al. | |
| 6,978,178 B2 | 12/2005 | Sommer et al. | |
| 7,011,633 B2 | 3/2006 | Strandberg | |
| 7,648,677 B2 * | 1/2010 | Santini et al. .................. | 422/50 |
| 2003/0009199 A1 | 1/2003 | Reinke et al. | |
| 2003/0074029 A1 | 4/2003 | Deno et al. | |
| 2003/0192784 A1 * | 10/2003 | Zhou ............................. | 205/109 |
| 2003/0204232 A1 | 10/2003 | Sommer et al. | |
| 2004/0172080 A1 * | 9/2004 | Stadler et al. .................... | 607/17 |
| 2004/0194302 A1 * | 10/2004 | Bhullar et al. ................... | 29/847 |
| 2005/0054939 A1 * | 3/2005 | Ben-Ari et al. ............... | 600/506 |
| 2005/0102024 A1 * | 5/2005 | Riccotta et al. .............. | 623/1.23 |
| 2005/0112544 A1 * | 5/2005 | Xu et al. ............................ | 435/4 |
| 2006/0100531 A1 | 5/2006 | Moser | |

(Continued)

FOREIGN PATENT DOCUMENTS

DE       195 07 929 A1   9/1996
WO    WO 95/26677 A   10/1995

(Continued)

OTHER PUBLICATIONS

European Search Report, EP 09 16 3885, Aug. 26, 2009.

*Primary Examiner* — Michael Kahelin
*Assistant Examiner* — Tho Tran
(74) *Attorney, Agent, or Firm* — Craig A. Fieschko, Esq.; DeWitt Ross & Stevens S.C.

(57) ABSTRACT

A device for the in vivo determination of the blood flow rate in a patient's blood vessel includes a microelectrode arrangement provided for placement in the blood vessel, an electrical power source which provides excitation energy having physiologically harmless parameters for obtaining a measured signal, a signal detector for detecting an electrical measured signal resulting from the blood flow in the presence of the excitation energy at measuring electrodes of the microelectrode arrangement, and a signal evaluation device, connected to the signal detector, for determining the blood flow rate on the basis of the measured signal.

26 Claims, 2 Drawing Sheets

(56) References Cited

U.S. PATENT DOCUMENTS

2007/0005114 A1* 1/2007 Salo et al. .................. 607/17
2008/0058630 A1* 3/2008 Robertson .................. 600/368
2008/0306359 A1 12/2008 Zdeblick et al.

FOREIGN PATENT DOCUMENTS

| WO | WO 02/053 026 A2 | 7/2002 | |
| WO | WO 2007/028035 A | 3/2007 | |
| WO | WO 2008036396 A2 * | 3/2008 | ............ A61F 2/46 |

* cited by examiner

DEVICE FOR DETERMINING THE FLOW RATE OF A BLOOD FLOW, AND CARDIOVASCULAR ASSIST DEVICE

FIELD OF THE INVENTION

The invention relates to a device and a method for the in vivo determination of the flow rate of a blood flow in a blood vessel. The invention further relates to a cardiovascular assist device which includes such a determination device.

BACKGROUND OF THE INVENTION

In human and veterinary medicine, considerable importance is attached to in vivo determination of blood flow rate because a sufficient flow rate is critical for vitality. In particular, the blood flow rate may be valuable for the detection of life-threatening stimulation states of the heart, and thus for controlling devices for assisting in the cardiovascular function, such as cardiac pacemakers or defibrillators.

Numerous sensors for the determination of flow rates are known from the art which are based on various measurement principles. These include, for example, sensors based on the Venturi or Bernoulli principle or the principle of Prandtl's pitot tube, as well as Doppler sonographic measuring systems. All of these systems are relatively technically complicated, and for most, their functionality in a living body is jeopardized by processes such as the growth of cells onto sensor components. Doppler sonographic measuring devices are also energy-intensive, and for this reason alone are not well suited for operation in the implanted state.

Using indirect methods, conclusions may also be drawn regarding blood movement in a living organism by use of pressure sensors, or other sensors which detect parameters that are a function of the blood flow. These include so-called hemodynamic sensors (HDS), or approaches which include intracardiac electrograms (IEGM). Such approaches are often relatively inaccurate and susceptible to malfunction.

A device is known from S. Gawad: "Micromachined impedance spectroscopy flow cytometer for cell analysis and particle sizing," Lab on a Chip, 2001, 1, 76-82, for classifying and sorting cells or particles in a liquid stream on the basis of their size. The device is used as a microelectrode arrangement which introduces electrical excitation energy into a liquid tube and detects a resulting impedance signal which is characteristic of the cells or particles flowing through.

Systems for measuring the blood flow in the heart or in blood vessels are also known which use two respective interspaced electrodes on an electrode line and a catheter, one of the electrodes being designed as a polarizable cathode, for simultaneously producing and detecting a galvanic cell potential which in principle is a function of the flow rate of the blood into the surroundings of the electrodes. U.S. Pat. No. 5,799,350 describes a corresponding system which may be inserted into the heart for measuring the blood flow rate in the vicinity of the cardiac valves. A similar measuring system, used as measurement electrodes for the stimulation electrodes of a pacemaker lead, is also known from U.S. Pat. No. 5,602,342. A similar measuring system which, as with the previously described system, may be used in a cardiac stimulator, is disclosed in U.S. Pat. No. 7,011,633 B2. This system is used as a measuring electrode for a ring-shaped, cylindrical, or spirally wound flat electrode whose inner surface is used as an active measuring electrode surface.

The latter-referenced systems have not become widely established in pacemaker treatment, probably as a result of their insufficient measurement accuracy.

SUMMARY OF THE INVENTION

An object of the present invention is to provide an improved device for the in vivo determination of the flow rate of a blood flow in a blood vessel, which in particular is comparatively uncomplicated and also functions with adequate accuracy and reliability over long periods of time. This object may be achieved by a device having features as set forth in the claims below, with a summary of preferred versions of the invention now being presented.

The invention assumes that adequate measurement accuracy is difficult to achieve for the known measuring systems which are based on an electrical measurement principle, due to the fact that they are not able to sufficiently differentiate between the signal-generating effect of convection and the signal-distorting effect of nondirectional diffusion on the measurement path between the inserted electrodes. In particular, the relatively large-area electrodes already provided on conventional pacemaker leads are not well-suited for use as measuring electrodes for this differentiation for the blood flow.

The invention makes use of the effect of convective diffusion caused by the flow of blood, which from an electrochemical standpoint is regarded as an electrolyte, in a blood vessel or in the heart, on an electrical signal present therein for drawing conclusions concerning the flow rate. The invention also includes the concept of inserting for this purpose microelectrodes into the blood vessel for introducing the electrical (excitation) signal into the flow path and connection to a suitable power supply. Lastly, a signal detector is connected to said microelectrodes (or also to other microelectrodes) for detecting said effect, and the detected electrical signal is evaluated using a suitable evaluation method.

Compared to known approaches, the invention offers important practical advantages: complex design measures as well as moving parts, which are present in many flow rate sensors, may be dispensed with altogether. Thus, problems which may arise from deposition of blood components on moving parts of a sensor over a long operating period of the measuring device are prevented from the outset. In addition, the operation may be carried out using less excitation energy than known methods, which allows comparatively long operation of the device as an essentially implantable measuring device with a self-contained battery.

Furthermore, the proposed measuring device may be advantageously combined with components of implantable devices for assisting in bodily functions, in particular cardiovascular assist devices and their associated electrode cables. This results in significant cost benefits and advantages in terms of insertion into the body of a patient.

In preferred designs the electrode system for the measuring device is characterized by miniaturization of the electrodes in order to minimize measurement errors. This miniaturization is made possible by means of microstructuring technology, i.e., using structuring methods known from semiconductor technology, and also allows integration of the electrode system with the signal detector, or at least means for signal preprocessing, on the same substrate (chip).

Special designs of the measuring device contain multiple microelectrode arrangements which are independently connected to the signal detector and optionally also to the electrical power source, and which therefore may represent essentially standalone sensors. A broad spatial distribution of such systems, if possible, makes the measuring device as a whole less sensitive to ingrowth processes due to the fact that a decreasing sensor function of a microelectrode arrangement as the result of ingrowth is partially compensated for by the still unimpaired functionality of other microelectrode arrangements. In one version of this design, a selection circuit is provided which on the basis of an external selection signal or the signals from an internal sensor system, which in particular are able to directly or indirectly detect the ingrowth state of the individual electrode systems, activates a selection of the (still) suitable sensors. In other words, unsuitable sensors are "switched off."

In one design, the invention provides that the surface area of the microelectrode arrangement is in a range between 100 and 10,000 $\mu m^2$, in particular between 200 and 5000 $\mu m^2$, and particularly preferably between 300 and 2000 $\mu m^2$. When a large number of individual small microelectrodes are connected to form an array, which is useful for obtaining a high total current, the lateral distance between individual measuring electrodes of the microelectrode arrangement is preferably at least three times, in particular at least five times, and particularly preferably at least seven times the corresponding lateral dimension of the individual electrode.

In a first version of the invention the microelectrodes are switched in a unipolar manner, whereby, for example, the electrodes of one or more surfaces switched in parallel are situated opposite one another (for example, on the device housing of a cardiac pacemaker or on the indifferent pole of a pacemaker probe). An alternative design provides a bipolar connection of the individual microelectrodes. In this case, for example two individual microelectrode arrangements, or such a system and a common counterelectrode, are situated opposite one another. In another version of the bipolar design, the opposite poles are each situated in close proximity to the individual electrode poles, and in one preferred design a gap which is as long and narrow as possible is provided between the electrode poles in the interests of high measurement accuracy. This may be achieved, for example, by a "coaxial" spiral configuration of the electrode and counterelectrode with a narrow gap in between, by intermeshed teething, or by a concentric configuration with an annular gap between an inner electrode (preferably very small) and an outer electrode which concentrically surrounds same. Electrodes can also be switched between measuring and excitation states.

Likewise in terms of informative value and accuracy of the measured values, it may be advantageous for the excitation electrodes and/or measuring electrodes to have a microstructured surface such that the contact surface area with the blood flow is a multiple greater than the geometric electrode surface area. In order to make the measured signals as independent as possible from interfering influences as the result of cardiac action potentials, the measuring electrodes are preferably situated coaxially on the conductor cable.

One practical design of the invention provides that the electrical power source is an alternating voltage source, and the signal detector has a measuring device for time-dependent measurement of a complex impedance between the measuring electrodes. Alternatively, the measuring device may operate in such a way that the electrical power source has a pulse generator for generating an excitation pulse sequence, and the signal detector has a measuring device for detecting a pulse response occurring at the measuring electrodes.

One design of the invention provides that the evaluation electronics system, and optionally also the excitation electronics system, is located in close proximity to the microelectrode arrangement, and is preferably integrated into a substrate in such a way that line connections are not necessary.

Thus, the excitation energy may be injected into the actual measuring device, for example via an induction coil which is structurally integrated therein. In the event that a signal detector cannot be placed in the immediate spatial proximity of the microelectrode arrangement but it is still desired to dispense with signal cables, it is suitable to use means for wireless signal transmission, for example so-called RFID (radio frequency identification).

In a further design of the invention, line connections are provided between the electrode system and the excitation energy source on the one hand and, in preferred designs, between the signal detector and/or the evaluation device on the other hand. In accordance with the above description, a design is possible in which the signal detector is in direct structural connection with the electrode system, so that there is no need for a line between same which is adapted to traverse a blood vessel. However, a line connection which runs in the blood vessel may be present between the signal detection device and the signal evaluation device.

Also useful is a design in which the electrical power source and the signal detector are situated in the housing of an implantable cardiovascular assist device, the first and the optional second line connection are situated in a conductor cable which may be connected to the assist device, and the microelectrode arrangement is situated on the surface of the conductor cable. Components which are well-known and established in pacemaker technology may be advantageously used for this purpose which are supplemented by the electrode system and the electronic components for signal detection and evaluation.

It may be provided in particular that the electrical power source and the signal detector are situated in the housing of a cardiac stimulator, and the line connection(s) and the microelectrode arrangement are situated in or on a stimulation electrode line. In addition, in this design the signal evaluation device may be situated in the housing of the assist device, in particular a cardiac pacemaker or defibrillator or a combination device.

However, the signal evaluation device may also be placed outside the body of the patient, for example to perform external monitoring or temporary investigation of the patient's hemodynamic state. The signal evaluation device may then be connected to the signal detection portion in the body via a telemetry path, for example, and in a bidirectional design this telemetry path may also be used to start and stop operation of the measuring device, and, if needed, to control specific parameters when a corresponding control unit is provided outside the body. In the fully implanted design, such a control unit may be provided in the housing of the implanted bodily function assist device.

Conversely, for such an integrated design of the measuring device with a bodily function assist device, an assist control unit for any device for controlling its assistance function is connected at the input side to an output of the signal evaluation device for the measuring device. Thus, for example, if it is determined that the flow rate drops below a predetermined threshold value, a conclusion is drawn that a life-threatening anomaly of the cardiac rhythm is present, and a corresponding antitachycardial pacemaker function or a defibrillator function of the assist device is automatically initiated.

To obtain sufficiently reliable measured values, it is advisably necessary on the one hand to take measures for maintaining a minimum distance from the vessel wall, and on the other hand (regardless of the relative insensitivity of the provided device in this respect) to take precautions against distorted measured values as the result of blood components growing onto the electrodes.

The desirable minimum distance depends to a certain extent on the surface area of the microelectrodes used, and on the basis of previous experience should be in the range of five to ten times the lateral extension of the microelectrodes.

The first-referenced measure may be achieved by providing suitable spacer elements on the electrode system, which for ease of insertion into the blood vessel advantageously have a retractable and extendable design, or a (preferably elastic) spreadable and foldable design. The latter-referenced measure is achieved by selecting a suitable metallic surface which does not promote the growth of biological material, or optionally by providing a specific growth-inhibiting coating.

Certain aspects of the aforementioned versions of the invention are inherent in, or evident in view of, the aforementioned discussion, and therefore these aspects are not discussed here. However, it is noted that in two basic alternatives the excitation energy is provided voltammetrically or potentiometrically, so that the measurement is performed as detection of current or voltage signals.

It is further noted that the excitation energy for the measurement process should be coordinated with the relevant pulse generation processes in the body of the patient to reliably prevent interference with the patient's bodily functions. Particularly important in this regard are the upper voltage or current limit values, which reliably prevent influence by the cardiac action potentials. For this purpose it is generally sufficient when the maximum amplitude of an excitation voltage or an excitation current is one-half the stimulation threshold of the human heart, in particular less than 50 mV, i.e., is associated with the occurrence of a voltage of less than 50 mV.

DETAILED DESCRIPTION OF PREFERRED VERSIONS OF THE INVENTION

Figure 1:
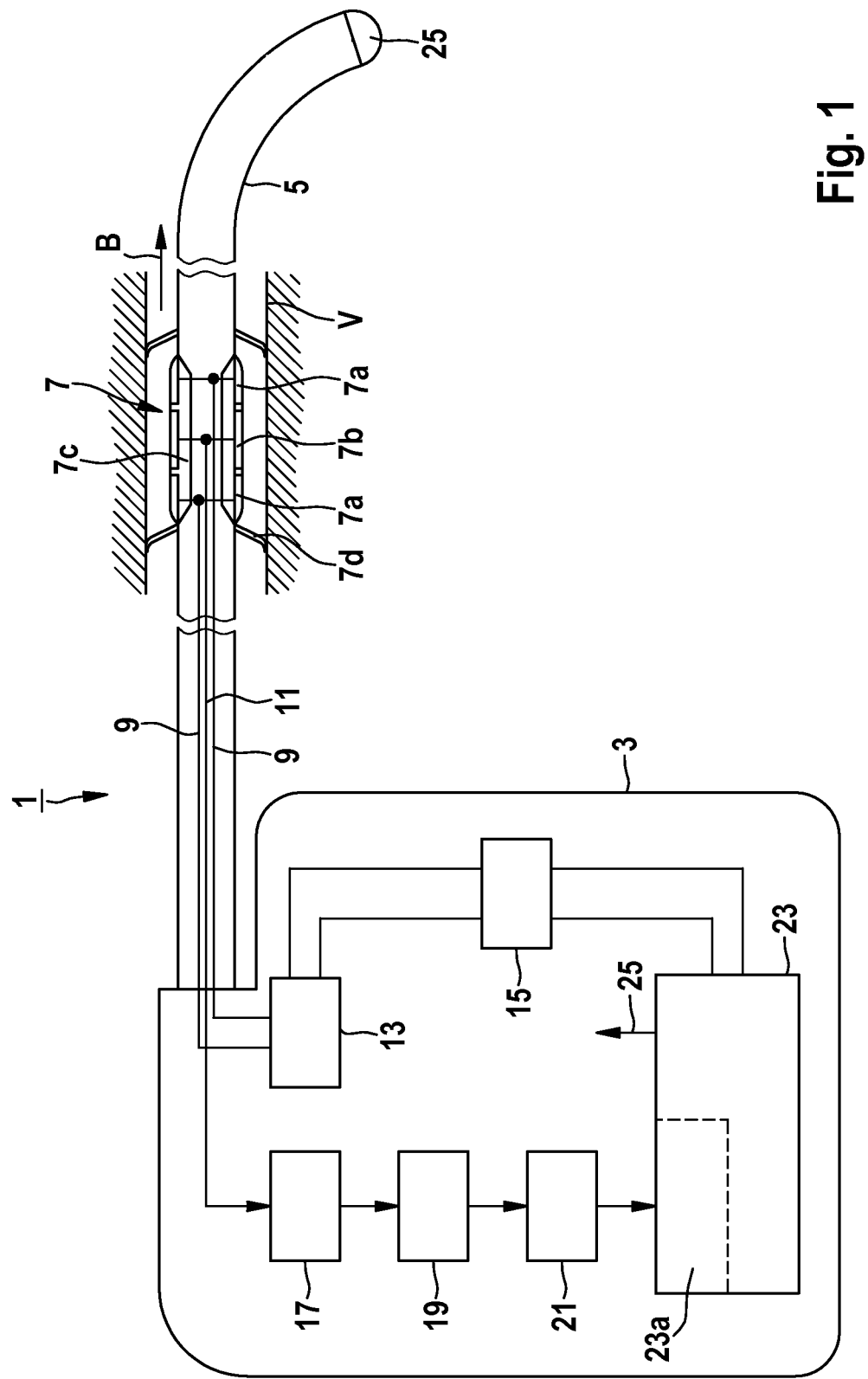
FIG. 1 illustrates a simplified, not-to-scale schematic illustration of one exemplary version of the invention in the manner of a functional block diagram, showing a fully implantable measuring device 1, which for the most part is structurally integrated with an antitachycardial cardiac pacemaker 3 or a stimulation electrode line 5 connected thereto which in places runs in a blood vessel V in which the flow rate of a blood flow B is to be measured with the cardiac pacemaker 3 and the electrode line 5.
Figure 2:
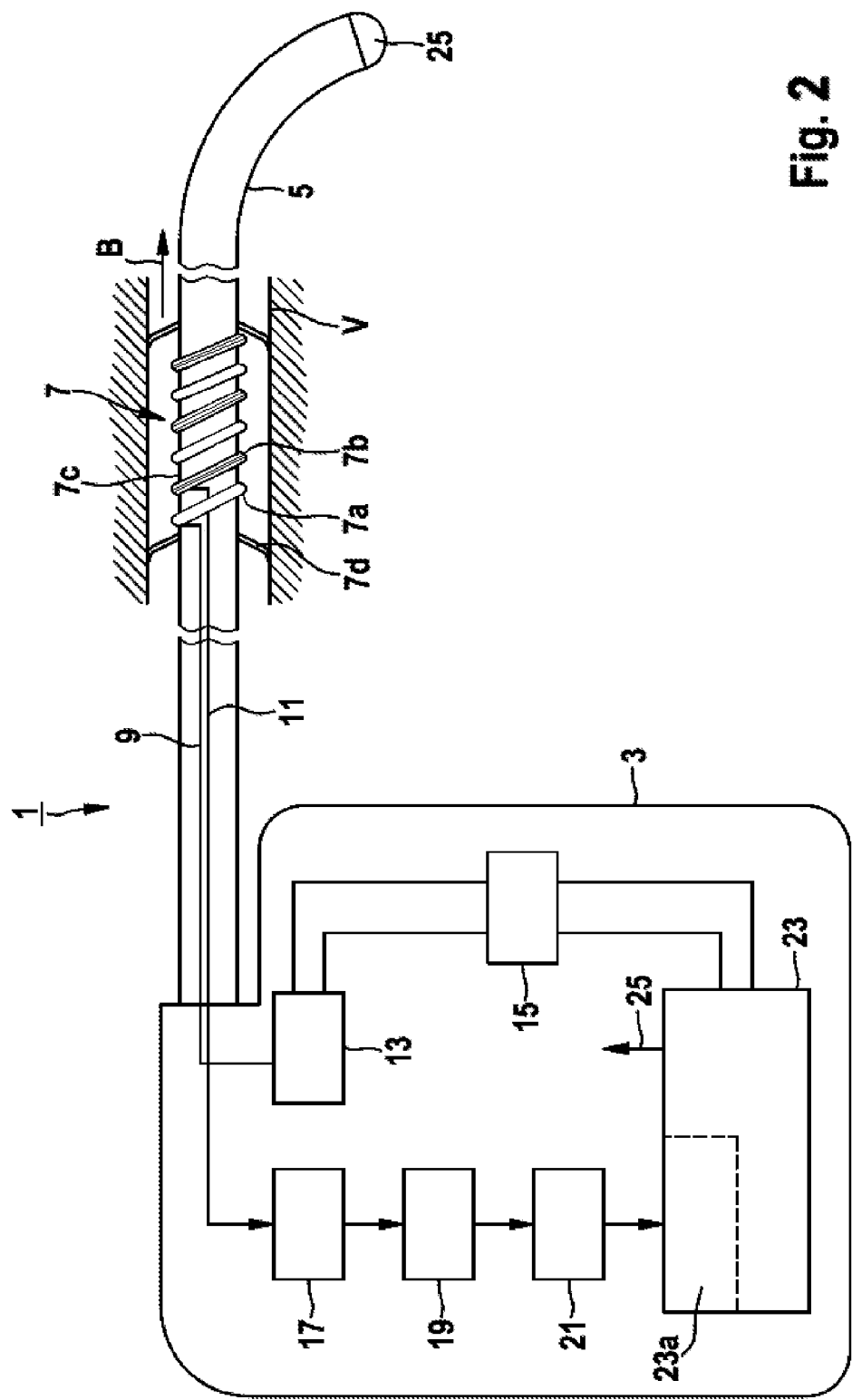
FIG. 2 illustrates an alternative version of the invention utilizing spiral excitation electrodes 7a and measuring electrodes 7b.

The measuring device 1 of FIG. 1 includes a microelectrode arrangement 7 which is coaxially situated on the circumference of the electrode line 5. The microelectrode arrangement 7 has multiple excitation electrodes 7a and measuring electrodes 7b provided on a substrate 7c by means of microstructuring technology. Multiple spacers 7d are associated with the electrode system 7, and are distributed around the circumference of the electrode line 5 to ensure sufficient spacing of the electrodes 7a and 7b from the wall of the blood vessel V in order to avoid distortion of measured values. To allow the electrode lines to be easily run through the blood vessel V despite these spacers 7d, the spacers 7d are preferably situated at an acute angle relative to the longitudinal axis of the electrode line and designed to be elastically pressed against the electrode line.

Electrical excitation energy (alternating or pulse voltage) is applied to the excitation electrodes 7a through supply lines 9, and via measuring lines (illustrated here as a single line 11). The measuring electrodes 7b pick up a (raw) measured signal which is induced by the excitation energy. The excitation energy is provided by an excitation energy source 13 in connection with a pacemaker battery 15. From the operating voltage provided by the battery 15, the excitation energy source 13 generates a low-amplitude alternating voltage or pulse signal, for example between 10 mV and 50 mV, which is sufficient for inducing a measured signal.

The measured signal is fed to a signal detection stage 17 in which a summation signal is formed from the measured values occurring at the individual measuring electrodes. In the case of excitation by alternating voltage the resulting alternating voltage signal (or for excitation by a pulse voltage, the induced pulse response) is detected as a time-dependent variable. On the output side the signal detection stage 17 is connected to an evaluation stage 19 in which the associated blood flow rate values are determined on the basis of the detected measured electrical signals using a previously stored evaluation algorithm.

On the output side the evaluation stage 19 is connected to a threshold value discriminator stage 21 in which any impermissibly low flow rate values which indicate a hemodynamically critical situation for the patient are detected using previously stored blood flow rate threshold values. On its output side the threshold value discriminator stage 21 is connected to a control input of a stimulation control stage 23a of a pacemaker electronics system 23. If the discriminator stage 21 generates a signal which indicates blood stasis or an impermissibly low blood flow rate, the stimulation control stage 23a initiates output of a stimulation pulse sequence to a stimulation electrode 25 at the tip of the electrode line 5. (For clarity, the signal connection between the two components of the pacemaker system 3/5 is not shown in its entirety in the figure.)

The implementation of the invention is not limited to this example or the aspects emphasized above; rather, the invention may also be implemented in a number of variations using skills of the art. It will be apparent to those skilled in the art that numerous modifications and variations of the described examples and versions are possible in light of the above teaching. The disclosed examples and versions are presented for purposes of illustration only. Therefore, it is the intent to cover all such modifications and alternate versions as may come within the true scope of this invention.

What is claimed is:

1. An implantable cardiovascular assist device providing in vivo determination of the blood flow rate in a bloodstream of a patient, the device including:
   a. an elongated electrode line including one or more stimulation electrodes for delivering stimulation pulses to a heart,
   b. multiple sets of microelectrodes configured for placement in the bloodstream,
      (1) the sets of microelectrodes being positioned spaced apart on the surface of the electrode line separate and spaced from the one or more stimulation electrodes,
      (2) each set of microelectrodes including at least one excitation electrode and at least one measuring electrode, each excitation electrode being spaced from one or more of the measuring electrodes by an elongated gap which is narrower than the electrode lengths of the spaced excitation and measuring electrodes, with the gap and the electrode lengths being measured along an axis bisecting the electrodes, c. an electrical power source connected to the excitation electrodes, the power source being configured to provide excitation energy,
d. a signal detector wherein:
   (1) each set of microelectrodes is independently connected to the signal detector, whereby each set delivers independently obtained measured signals to the signal detector, and
   (2) in the presence of the excitation energy, the signal detector detects an electrical measured signal at the measuring electrodes resulting from the blood flow, and
e. a signal evaluation device in communication with the signal detector, the signal evaluation device being configured to determine the blood flow rate on the basis of the measured signal.

2. The device of claim 1 wherein:
a. the microelectrodes include at least two measuring electrodes,
b. the power source includes an alternating voltage source wherein alternating voltage is provided as excitation energy to the excitation electrodes, and
c. the signal detector performs time-dependent measurement of a complex impedance between two or more measuring electrodes.

3. The device of claim 1 wherein the power source includes a pulse generator for generating an excitation pulse sequence, wherein the excitation pulse sequence is provided as excitation energy to the excitation electrodes.

4. The device of claim 1 wherein at least one of the electrodes is switchable to alternate between service as a measuring electrode and an excitation electrode.

5. The device of claim 1 wherein at least one of the excitation electrode and the measuring electrode:
a. is bounded by a perimeter, wherein the electrode has a geometric electrode area defined within the perimeter; and
b. has a surface area configured to be in contact with the blood flow wherein the surface area is at least twice as large as the geometric electrode area.

6. The device of claim 1 wherein the microelectrodes collectively have a surface area between 300 and 2000 square micrometers.

7. The device of claim 1 wherein:
a. the microelectrodes include at least two measuring electrodes,
b. each measuring electrode is spaced from all other measuring electrodes by at least three times the largest dimension of the measuring electrode, as measured from one side of the measuring electrode's perimeter to the opposing side of the measuring electrode's perimeter.

8. The device of claim 1 wherein the power source and the signal detector are situated in a housing of the implantable cardiovascular assist device.

9. The device of claim 1 further including a selection circuit selectively:
a. enabling one or more of the sets of microelectrodes, and
b. disabling one or more of the sets of microelectrodes wherein the signals obtained therefrom are indicative of overgrowth of one or more of the electrodes therein.

10. The device of claim 1 wherein the microelectrodes:
a. include at least two excitation electrodes, and
b. are arrayed with each pair of excitation electrodes spaced along the length of the electrode line with a single measuring electrode situated therebetween.

11. The device of claim 1 wherein the excitation electrodes and the measuring electrodes have spiral shapes.

12. The device of claim 1 wherein the excitation electrodes and the measuring electrodes are spaced by a narrow annular gap.

13. The device of claim 1 wherein the excitation electrodes and the measuring electrodes are defined by intermeshing teeth.

14. The device of claim 1 further including one or more spacers situated adjacent the microelectrodes and extending outwardly therefrom, whereby the one or more spacers maintain the microelectrodes at a distance from a wall of a blood vessel when the microelectrodes are inserted into the blood vessel.

15. The device of claim 14 wherein the spacers are aligned at an acute angle relative to a longitudinal axis of the electrode line.

16. The device of claim 14 wherein the spacers are elastically biased away from the electrode line.

17. The device of claim 1 wherein the cardiovascular assist device is a cardiac pacemaker and/or a defibrillator configured to deliver stimulation to a heart at least partially in response to the blood flow rate determined by the signal evaluation device.

18. A cardiac pacemaker and/or defibrillator including:
a. an elongated electrode line having a line surface bearing:
   (1) one or more stimulation electrodes for delivering stimulation pulses to a heart,
   (2) one or more excitation electrodes, each excitation electrode being a microelectrode:
      i. spaced from each stimulation electrode, and
      ii. in communication with an electrical power source configured to provide excitation energy to the excitation electrode,
   (3) one or more measuring electrodes, each measuring electrode being a microelectrode:
      i. spaced from each stimulation electrode,
      ii. spaced from each excitation electrode by a gap which is narrower than the electrode lengths of the spaced measuring and excitation electrodes, with the gap and electrode lengths being measured along an axis bisecting the measuring and excitation electrodes, and
      iii. in communication with a signal detector, wherein in the presence of the excitation energy, the signal detector detects an electrical measured signal at the measuring electrode resulting from any blood flow adjacent the measuring electrode, and
   (4) spacers extending outwardly from the line surface, whereby the spacers space the line surface at a distance from a wall of a blood vessel when the electrode line is inserted into the blood vessel;
b. a signal evaluation device in communication with the signal detector, the signal evaluation device being configured to determine the blood flow rate adjacent one or more of the measuring electrodes on the basis of the measured signal.

19. The device of claim 18 wherein the excitation electrodes and the measuring electrodes have spiral shapes.

20. The device of claim 18 wherein:
a. the microelectrodes include at least two measuring electrodes,
b. the power source includes an alternating voltage source wherein alternating voltage is provided as excitation energy to the excitation electrodes, and
c. the signal detector performs time-dependent measurement of a complex impedance between two or more measuring electrodes.

21. The device of claim 18 wherein at least one of the electrodes is switchable to alternate between service as a measuring electrode and an excitation electrode.

22. The device of claim 18 wherein:
   a. the microelectrodes include at least two measuring electrodes,
   b. each measuring electrode is spaced from all other measuring electrodes by at least three times the largest dimension of the measuring electrode, as measured from one side of the measuring electrode's perimeter to the opposing side of the measuring electrode's perimeter.

23. The device of claim 18 further including a selection circuit selectively:
   a. enabling one or more of the sets of microelectrodes, and
   b. disabling one or more of the sets of microelectrodes wherein the signals obtained therefrom are indicative of overgrowth of one or more of the electrodes therein.

24. The device of claim 18 wherein the microelectrodes:
   a. include at least two excitation electrodes, and
   b. are arrayed with each pair of excitation electrodes spaced along the length of the electrode line with a single measuring electrode situated therebetween.

25. The device of claim 1 wherein the power source is configured to provide excitation energy to both the excitation electrodes and the measuring electrodes.

26. The device of claim 1 wherein:
   a. the excitation energy is defined by time-varying voltage, and
   b. the electrical measured signal is defined by a complex impedance.

* * * * *